United States Patent
Vincent et al.

[11] Patent Number: 5,540,808
[45] Date of Patent: Jul. 30, 1996

[54] ENERGY DIRECTOR FOR ULTRASONIC WELDING AND JOINT PRODUCED THEREBY

[75] Inventors: Douglas E. Vincent, Manchester, N.H.; Kevin A. Durand, Lancaster, Mass.

[73] Assignee: DEKA Products Limited Partnership, Manchester, N.H.

[21] Appl. No.: 380,307

[22] Filed: Jan. 30, 1995

Related U.S. Application Data

[62] Division of Ser. No. 22,019, Feb. 24, 1993, Pat. No. 5,401,342.

[51] Int. Cl.⁶ ................................................. B32B 31/00
[52] U.S. Cl. ...................................... 156/580.2; 156/73.1
[58] Field of Search ............................. 156/73.1, 580.2

[56] References Cited

U.S. PATENT DOCUMENTS

| | | | |
|---|---|---|---|
| 240,916 | 5/1881 | Maxwell | D25/23 |
| 3,602,257 | 8/1979 | Berleyoung | 137/594 |
| 3,973,064 | 8/1976 | Paine | 428/60 |
| 4,230,757 | 10/1980 | Toner | 428/137 |
| 4,301,343 | 11/1981 | Jonelis | 200/283 |
| 4,396,562 | 8/1983 | Heaume | 264/23 |
| 4,558,957 | 12/1985 | Mock et al. | 368/294 |
| 4,631,685 | 12/1986 | Peter | 364/476 |
| 4,907,513 | 3/1990 | Manion et al. | 102/527 |
| 5,073,216 | 12/1991 | Siegel et al. | 156/73.3 |
| 5,088,515 | 2/1992 | Kamen | 137/15 |
| 5,114,513 | 5/1992 | Hosokawa et al. | 156/150 |
| 5,269,917 | 12/1993 | Stankowski | 210/232 |

FOREIGN PATENT DOCUMENTS

| | | | |
|---|---|---|---|
| 60-248336 | 12/1985 | Japan | 264/23 |
| 5-16241 | 1/1993 | Japan | 264/23 |

OTHER PUBLICATIONS

"Plastics Assembly News—Application Brief #56—Ultrasonic Welding with Roughened Surface", Branson Ultrasonics Corporation, 1989.
"Ultrasonic Welding Characteristics of Textiles and Films", Branson Ultrasonics Corporation, 1981/1989.
Selections of "Ultrasonic Plastics Assembly", Branson Ultrasonics Corporation, 1979.
"Design Parts for Ultrasonic Welding", Branson Ultrasonics Corporation, 1980/1989.

*Primary Examiner*—Chester T. Barry
*Attorney, Agent, or Firm*—Bromberg & Sunstein

[57] ABSTRACT

A process is provided for ultrasonically welding a rigid thermoplastic, such as acrylic, and a flexible thermoplastic, such a polyvinyl chloride (PVC) doped with plasticizers. The rigid piece includes an energy director where the joint is to be located. The energy director includes first and second ridges running the length of the joint and a groove running between the first and second ridges. The energy director is placed against one side of the flexible piece, and an ultrasonic horn against the other side opposite the energy director. The two pieces are then welded together using standard ultrasonic technology. The shape of the energy director promotes the melting and flow of both pieces as they are being welded together.

4 Claims, 5 Drawing Sheets

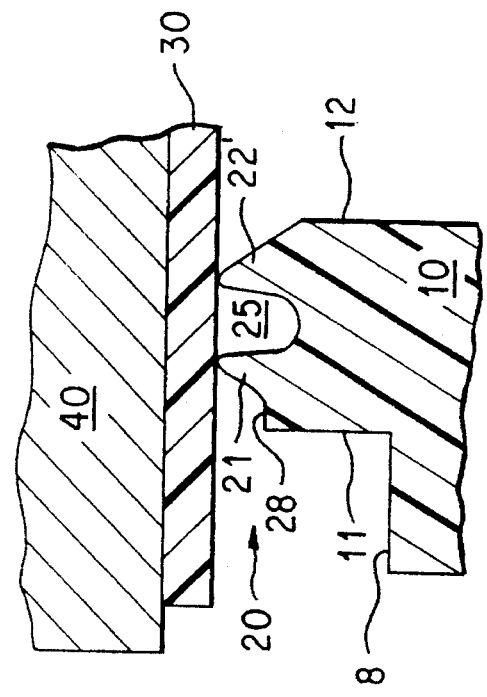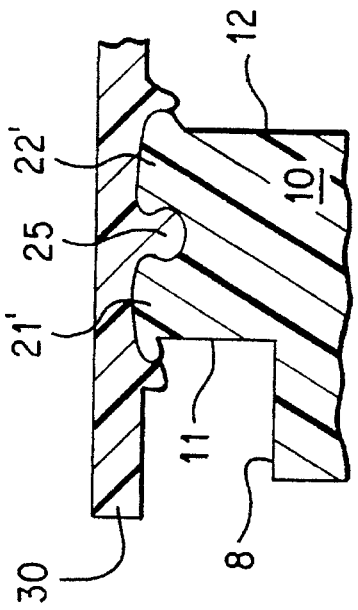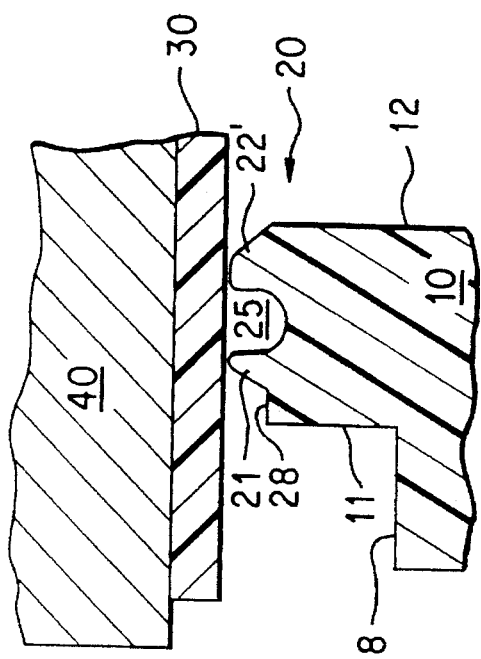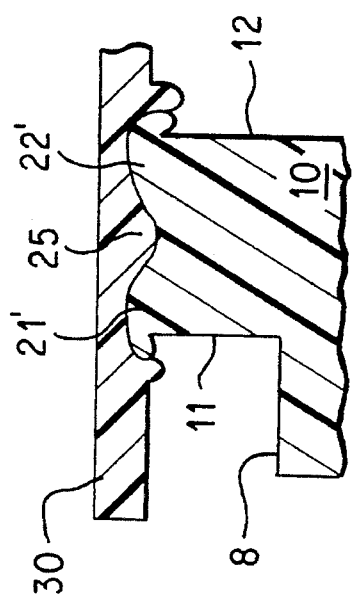

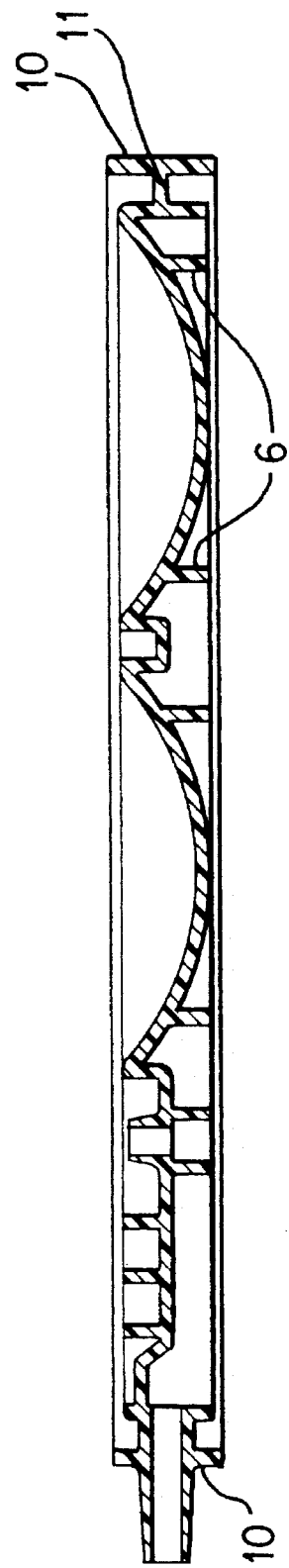
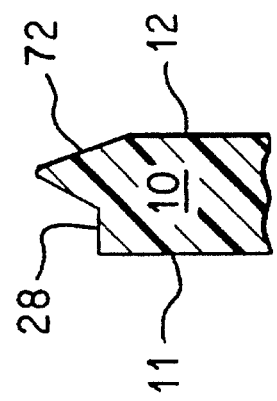
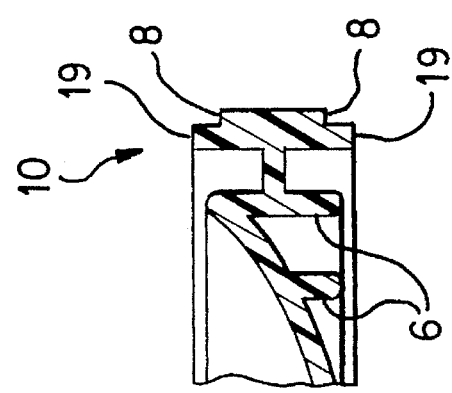
FIG. 8
FIG. 10
FIG. 9

5,540,808

ENERGY DIRECTOR FOR ULTRASONIC WELDING AND JOINT PRODUCED THEREBY

This application is a divisional of application Ser. No. 08/022,019 filed on Feb. 24, 1993, now U.S. Pat. No. 5,401,342.

TECHNICAL FIELD

This invention generally relates to methods and apparatuses for ultrasonically welding two materials together, particularly a flexible material, such as polyvinyl chloride with plasticizers, and a rigid material, such as acrylic.

BACKGROUND ART

Ultrasonic welding has long been used to join together two thermoplastic pieces. Prior to the present invention, it had been thought that materials having different properties, such as a rigid piece and a flexible piece, were generally not suitable for being ultrasonically welded together. It had also been thought that it was difficult to ultrasonically weld plasticized polyvinyl chloride with good results, especially to another type of material.

Energy directors have been used to improve ultrasonic welding. These prior art energy directors typically have a single peak, which is sometimes roughened for particular applications.

SUMMARY OF INVENTION

One aspect of the invention is directed to a process for joining first and second pieces together. In a preferred embodiment, the first piece is a rigid thermoplastic, such as acrylic, and the second piece is a flexible thermoplastic, such as polyvinyl chloride (PVC) doped with plasticizers, which make the PVC flexible. The invention is also directed to an energy director used in the process, and the joint formed between the two pieces by the welding process.

The first piece includes an energy director located where the joint is to be formed between the first and second pieces. The energy director includes first and second ridges running the length of the joint and a groove running between the first and second ridges. The second piece is preferably flat, having two sides.

The energy director is placed against one side of the second piece, and an ultrasonic horn against the other side opposite the energy director. The two pieces are then welded together using standard ultrasonic technology, i.e., by using the horn to apply vibrations to the second piece.

It is an aim of the energy director to promote the melting and flow of both pieces as they are being welded together. As a result of the ultrasonic welding, the ridges become flattened, but nevertheless protrude into the flexible material. A portion of the flexible material protrudes into the groove of the rigid piece. In one preferred embodiment, at least one of, and preferably both of, the ridges are of sufficient height and sufficient narrowness, and the groove is of sufficient depth, that when the wall is ultrasonically welded to the second piece, he second material can flow into the groove, and the ridge or ridges can spread so as to overlap some of the material of the second piece in the groove.

The energy director may further include a ledge, adjacent one of the first and second ridges opposite the groove and the other ridge, so as to limit how far the horn may advance during welding. In one embodiment, the outer side of the ridge opposite the ledge slopes all the way down to the side of the wall on which the energy director is placed, preferably meeting the side of the wall at a point below the ledge. An alternative energy director uses only a single ridge that has a slope that goes all the down to the side of the wall, preferably down to a point below a ledge on the opposite side of the ridge.

BRIEF DESCRIPTION OF THE DRAWINGS

FIGS. 1A and 1B each show a cross-section of two pieces to be welded together and the ultrasound horn just prior to welding.

FIGS. 2A and 2B each show a cross-section of the two pieces after welding, wherein FIG. 2A shows a result of the arrangement shown in FIG. 1A, and FIG. 2B shows a result of the arrangement shown in FIG. 1B.

FIG. 8 shows a cross-section of the rigid cassette portion shown in FIG. 6.

FIG. 9 shows a detail of a cross-section of an alternative embodiment of the rigid cassette portion.

FIG. 10 shows a cross-section of an alternative energy director.

DESCRIPTION OF SPECIFIC EMBODIMENTS

Figure 3:
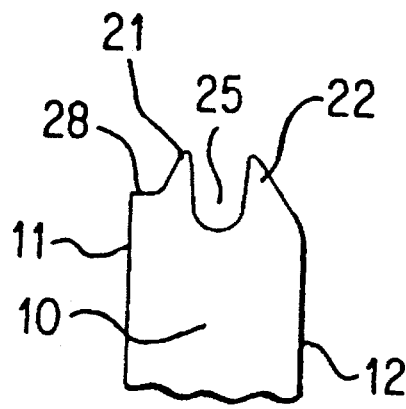
FIGS. 3–5 show various embodiments of the energy director according to the present invention.

FIGS. 1A, 1B, 2A and 2B show how a flat, flexible piece 30 of thermoplastic material, such as PVC doped with plasticizers, may be ultrasonically welded to the edge of a rigid piece 10 of thermoplastic material, such as acrylic. The preferred method of ultrasonic welding is very-near-field plunge-type high-amplitude welding. The horn 40 is placed on one side of the flexible membrane 30, and the energy director 20 of the rigid piece 10 is placed opposite the horn 40 on the other side of the membrane 30.

The horn 40, which may be an EDP# 109-115-008 (aluminum or titanium) made by the Branson Ultrasonics Corporation, Danbury, Conn., is attached to a booster, which in turn is attached to a converter, such as the model 900M with a 921aes intelligent actuator also made by Branson Ultrasonics. The converter turns high frequency (20,000 Hz) AC electrical power into mechanical vibrations. The booster amplifies the amplitude of the vibrations by a certain multiple, e.g. 2.5 times. Boosters of different gains may be used instead. A booster producing vibrations of a lower amplitude, such as a 2 times booster, may be preferable, since it causes less stress on the horn, giving the horn a longer life. A continuously variable de-amplifier may be used to reduce the amplitude of the ultrasonic vibrations, in order to obtain a net amplification that is not otherwise available using standard booster horns.

The energy director 20 is an integral part of the rigid piece 10 and may be molded as part of the rigid piece 10 at the same time that the rigid piece 10 is molded. The portion of the rigid piece 10 that has the energy director 20 is preferably a wall, with the energy director 20 located on the wall's top (or bottom). The energy director includes two ridges 21 and 22 and a groove 25 located between them. The ridges 21 and 22 and the groove 25 run along the length of the wall 10.

The energy transmitted by the horn 40 causes the flexible membrane 30 to melt, and some of the material of the flexible membrane 30 flows into the groove 25 of the energy director 20. Acrylic normally has a higher melting point than plasticized PVC. However, the shape of the energy director 20, in particular the tapering of the ridges 21 and 22 to a fairly narrow point, promotes melting at the tips of the ridges 21 and 22. As a result the ridges 21 and 22 flatten out, so that, in one preferred embodiment, portions of the flattened-out ridges 21' and 22' overlap portions of the membrane material in the groove 25.

In the preferred designs, such as those shown in FIGS. 1A, 1B and 3-5, one side of each ridge 21 and 22—the side adjacent the groove 25—is very steep, almost vertical. If the ridges 21 and 22 are tall enough and the groove 25 is deep enough, as in FIGS. 1B and 3, this steepness promotes "mushrooming" of the ridge on that side during welding; in other words, it promotes the protrusion of the ridge in a horizontal direction so that it could overlap some of the material of the membrane 30 that has flowed into the groove 25 during welding. Even if the groove 25 is not so deep, as in FIGS. 1A and 4, the steepness of the sides of the ridges 21 and 22 nearer the groove 25 helps promote some flow of the rigid material 10 towards the groove 25 during welding. (If the sides of the ridges 21 and 22 nearer the groove 25 were formed so that they already leaned over the groove 25 before the welding even began, mushrooming could be promoted even further; however, it would be much more difficult to form such an energy director along the length of a wall using standard injection molding, and would therefore be much more expensive to make.) To make the ridges 21 and 22 less fragile, the sides of the ridges further from the groove 25 may be made less steep, as shown in FIGS. 1A, 1B and 3-5. Making the ridge sides further from the groove 25 less steep than the nearer sides also promotes the flow of melted rigid material towards the groove 25 during welding.

Figure 6:
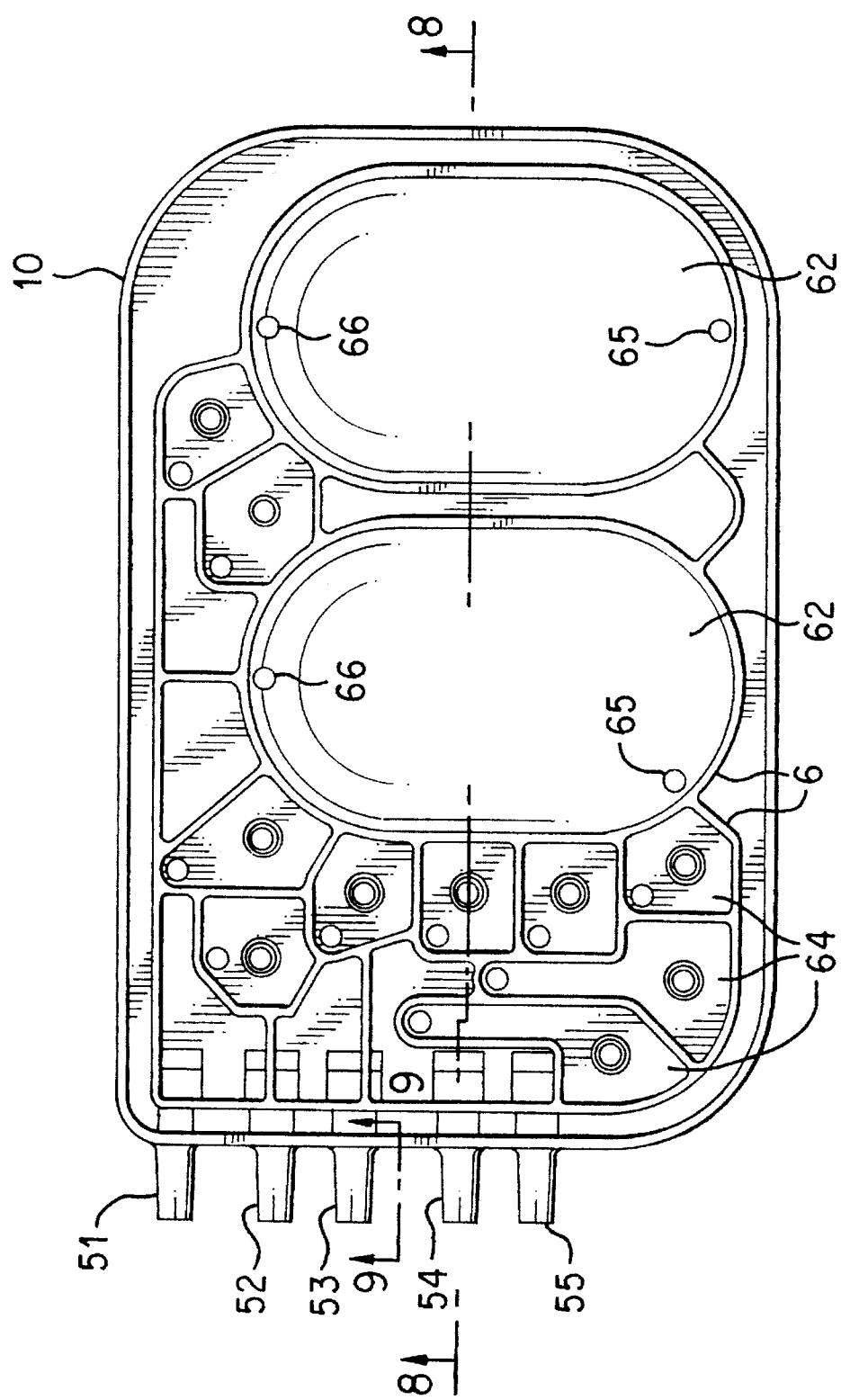
FIG. 6 shows a front plan view of the rigid portion of a disposable parenteral-fluid cassette that may use the invention along its outer wall.
Figure 7:
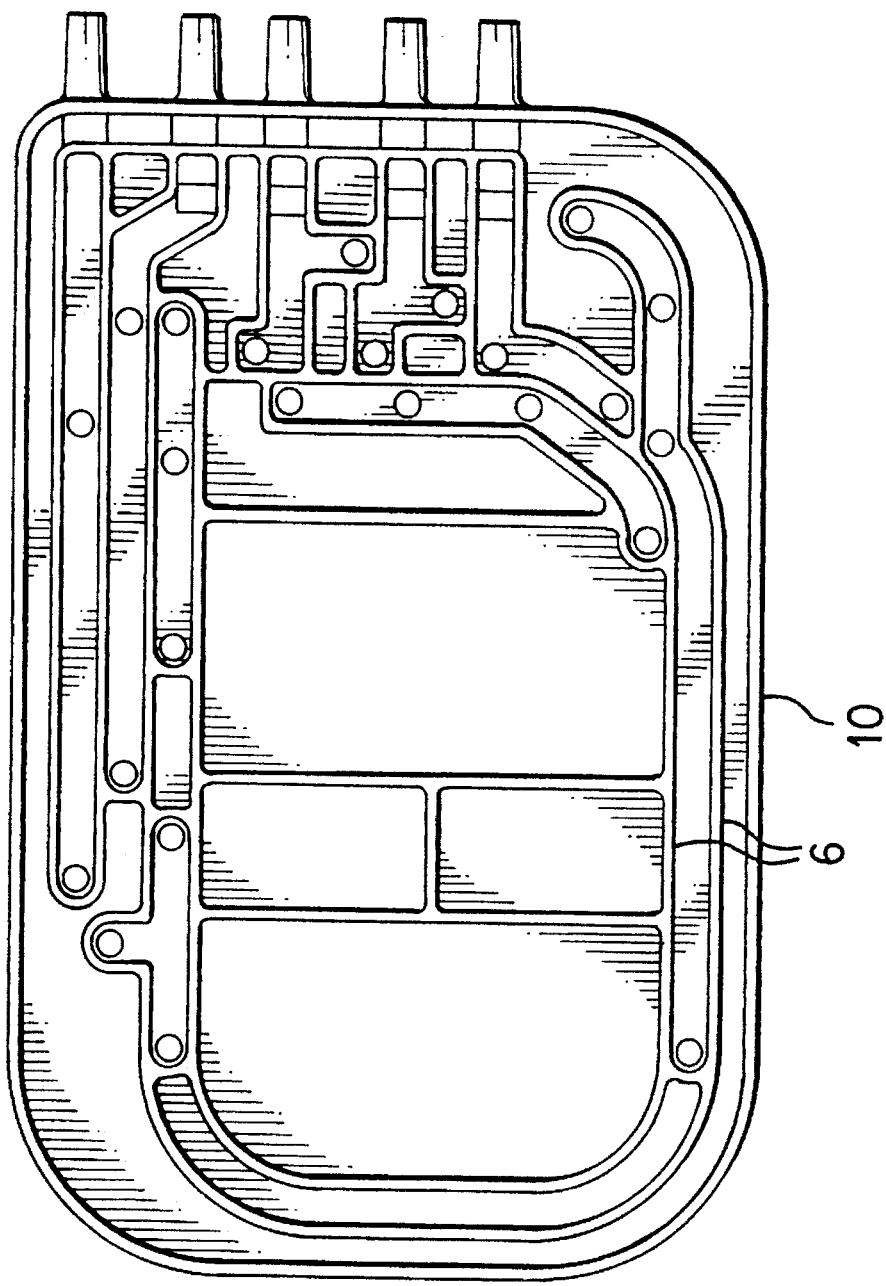
FIG. 7 shows a rear plan view of the rigid cassette portion shown in FIG. 6.

Although the terms "vertical" and "horizontal" are used herein to describe what is shown in the figures, and although ultrasonic welders are typically oriented so that the horn is above the items to be welded, it will be appreciated that the ultrasonic welding can be performed in a variety of orientations. In the preferred version of the process, the horn 40 is above the membrane 30, while the rigid portion 10 is below it. (The preferred orientation during actual use of the disposable peritoneal dialysis cassette discussed below and shown in FIGS. 6-8 is for the inlet/outlet mouths 65 and 66 of the pressure-conduction chambers 62 to be on the top and the bottom—the mouths leading to two of the cassette nozzles 51 and 52 being on top, and the mouths leading to three cassette nozzles 53, 54 and 55 being on the bottom. This orientation makes it easier to expel air from the cassette through the nozzles 51 and 52, which are normally connected to the heater and the drain in the automated peritoneal dialysis system. The remaining three nozzles 53, 54 and 55 are connected to two alternative fluid supplies and the patient.)

One advantage of the energy director structures shown in FIGS. 1A, 1B and 3-5 is that they slow the welding process (as compared to an energy director that had only a single ridge), thereby allowing greater intermingling of the melted rigid material 10 and the melted flexible material 30 during welding. It is important for obtaining a strong joint between the two materials that, during welding, both materials melt and sufficient flow occurs between the melted materials, so that when the welded area cools a large surface area exists between the two materials. It is believed that intermingling of the rigid material 10 and the flexible material 30 results in some type of micro-mechanical connections between the flexible membrane and the rigid portion 10, similar perhaps to hook-and-loop connectors. In some embodiments, such as the one shown in FIGS. 1B and 2B, the flattened ridges 21' and 22' pinch on that portion of the membrane material in the groove 25. There may also be some chemical bonding between the membrane 30 and the rigid portion 10. The two-ridge energy director structure also increases the contact area between the rigid portion 10 and the flexible membrane 30 during and after welding. Increased contact area provides a stronger bond between the two materials.

Furthermore, the slowing of the welding process gives a larger tolerance for the welding parameters, in particular, the length of time and the intensity of the welding should be performed. For instance, if the welding does not last long enough, the desired amount of bonding may not occur. On the other hand, if the welding lasts too long, then the horn 40 may press down too far and leave the membrane 30 too thin or cut all the way through the membrane. If only a single ridge is used, the welding process moves more quickly, and the weld must have just the right amplitude and be timed just right, otherwise the membrane 30 may be cut or may not be adequately bonded to the rigid portion. By slowing the welding by using two ridges 21 and 22, a greater tolerance for weld time and intensity is permitted. This greater tolerance is especially important where the rigid wall 10 has straight sections and curved sections or corners—such as the disposable cassette discussed below and shown in FIGS. 6-8—because the welding behaves differently in straight and curved sections of the wall 10, and because, in a preferred embodiment of the process, the entire joint connecting the rigid portion of the cassette to the flexible membrane 30 on one side of the cassette is welded to at the same time. (See discussion below.) If an energy director having only a single ridge were used, so that there was less tolerance to the weld time and intensity, attempting to weld a wall having straight and curved sections could result in some sections of the membrane being welded too much, thereby resulting in the membrane being too thin or perhaps even cut in those sections, while other sections are properly welded or perhaps not even welded enough. Using an energy director having a large tolerance for weld time and intensity makes it much easier to provide satisfactory bonding all around the wall FIGS. 2A and 2B show representative cross-sections of the welded joints created by the arrangements of FIGS. 1A and 1B respectively. The exact shape of the welded joint will of course vary from weld to weld and even within a given device—in particular the weld cross-sections will look different in a straight section of the wall 10 from the weld cross-section in a curved section.

FIG. 2B, which shows the membrane 30 and rigid portion 10 of FIG. 1B after having been welded together, shows the pinching of the flattened ridges 21' and 22' on that portion of the membrane material that has flowed into the groove 25. This pinching action provides a stronger connection between the rigid and flexible pieces. Both of the joints shown in FIGS. 2A and 2B provide a durable connection and a hermetic seal between the flexible membrane 30 and the rigid portion 10.

The process described herein provides around the edge of the cassette a durable hermetic seal. Such a seal along the cassette's perimeter wall is useful in many applications, but can be especially important in order to insure that the interior of a disposable medical-fluid cassette—through which peritoneal, intravenous or other parenteral fluid may flow—remains sterile during storage. An example of such a disposable parenteral-fluid cassette is shown in U.S. Pat. No. 5,088,515 issued Feb. 18, 1991 to Kamen or in U.S. patent application Ser. No. 07/614,806 filed Nov. 19, 1990 for an invention of Kamen (now abandoned in favor of a file-wrapper continuation application Ser. No. 07/908,524, filed Jun. 29, 1992).

FIGS. 6–8 herein show the rigid portion of a disposable parenteral-fluid cassette, similar in function to those shown in FIGS. 3–5 and 7 of U.S. Pat. No. 5,088,515. This cassette may be used in an automated peritoneal dialysis system. The cassette has flexible membranes attached to the front and rear of the rigid portion. The energy director 20 may be placed along both ends 19 of the perimeter wall 10 of the cassette shown in FIGS. 6–8 herein, so that membranes may be attached on both the rear and the front of the rigid portion of the cassette.

In a preferred embodiment of the process, a membrane is first welded to the front of the rigid portion of the cassette, then this membrane is trimmed, then a second membrane is welded to the rear of the cassette's rigid portion, and then the rear membrane is trimmed. For the welding of the front membrane, a locator is used to position and hold the cassette for welding. The rigid portion is laid on top of a sheet of silicone in the locator. The silicone sheet serves to protect the energy director on the rear side, so that the rear energy director will not be unduly deformed when the front membrane is welded onto the cassette. In addition, the silicone sheet permits the front face (i.e., the top of the rigid portion during welding) of the rigid portion 10 to become parallel to the bottom face of the horn 40 during welding, even if the rigid portion was not molded properly so that both faces of the rigid portion are perfectly parallel to each other. A third benefit of using a silicone sheet under the rigid portion during welding is that it helps reduce the occurrence and the effect of nodes (dead spots) along the joint being welded. (Nodes can result in weak welds or unwelded portions at points along the joint between the two materials.) After the front sheet is welded and trimmed, the cassette is turned over and placed in another welder for welding the rear membrane, so that, during welding of the rear membrane, the front membrane is on the bottom. A silicone sheet is also placed under the front side of the cassette when the rear membrane is being welded to the rear face of the rigid portion. The bottom face of the horn 40 used for the cassette shown in FIGS. 6–8 is a rectangle, having dimensions of about 4.94×6.32 inches, so that it is a little larger than the cassette. (Preferably, two separate but identical horns are used for welding the front and rear membranes to the cassette.) In lieu of a sheet of silicone placed in the locator, a groove corresponding to the outer 10 wall of the cassette may be etched into the locator and filled with silicone, so that the silicone is located under just the outer wall 10 of the cassette. This gasket-like strip of inlaid silicone, like the sheet of silicone, acts as a cushion for the welding of either side of the cassette Some of variables of the welding process are weld time, weld pressure, amplitude, velocity, hold time and trigger force. The first three of these variables—weld time, weld pressure and amplitude-have been found to be more critical to achieving a good weld than the last three—velocity, hold time and trigger force. Weld time is how long the ultrasonic vibrations are applied to the joint and can be measured by time or by how much energy is to be transmitted by the horn before being turned off. It has been found that having the weld last between 1 and 1.5 seconds or until about 1,000 joules have been transmitted has good results for the present application. Weld pressure is how much force (per unit of area) the horn 40 applies to the membrane during the welding, and a weld pressure of 20–25 psig has had good results. Amplitude is the amplitude of the vibrations created by the horn. The amplitude is determined by the booster, which as noted above may be a 2.5:1 booster or alternatively a 2:1 booster. A continuously variable de-amplifier may be used with the 2.5:1 booster in order to obtain a net amplification between 2 and 2.5. The velocity is the speed of the horn 40 coming down onto the membrane to start the welding. A high velocity allows more welds to be made by the same machine during a given period of time, but can also cause too much stress in the joint. A velocity in the range of about 1–10 inches/second may be used. After the horn, which is moved downward by a pneumatic system, comes into contact with the membrane, it continues to press downward and turns on once the trigger force is reached. A trigger force of about 10 pounds has been found to have good results. Hold time is how long the horn remains pressed against the joint after it has been turned off, and a hold time in the range of about 0.5–1.5 seconds has had good results. Of course, it may be necessary to modify some or all of these values in applications that are different from the disposable cassette described herein, e.g., if different materials are used, or if the dimensions of the components being welded together are different, or if the energy director is of a different design. The foregoing values were used with the energy director shown in FIGS. 1A and 4.

When the rear membrane is welded to the rigid portion, the rigid portion rests on the front membrane, which has already been attached to the rigid portion, and on a silicone sheet (or the inlaid, gasket-like silicone cushion). This results in somewhat different dynamics in the welding of the front and rear sides of the cassette. It has been found to be beneficial to have different values for some of the foregoing variables for welding the front and rear membranes. The following values have been used and have had good results: a weld pressure of 20.5 psig for the front membrane and 22 psig for the rear membrane, a weld time of 1.2 seconds for the front and 1.3 seconds for the rear, a hold time of 0.625 seconds for the front and 0.75 seconds for the rear, and a horn velocity of 4.5 inches/second for the front and 6.0 inches/seconds for the rear.

The materials that have been found by the inventors to bond-well together using the foregoing process are, for the rigid portion, an acrylic, in particular HFI-10G Plexiglas® by Rohm and Haas, and for the flexible membrane, a plasticized PVC, in particular PL 146® by Baxter International. This plasticized PVC is inexpensive, available in large quantities and already in wide use for containing medical fluids, thereby making it desirable for use as the flexible membrane in a disposable parenteral-fluid cassette. Preliminary tests indicate that other thermoplastics may be substituted for these materials. For example, polycarbonate and ABS (acrylonitrile-butadiene-styrene) may be used for the rigid portion, and polyurethane for the flexible portion.

Since, in the preferred embodiment of the cassette, the membrane is ultrasonically welded to just the perimeter of the cassette, some other means is necessary for sealing the various fluid passageways (including the valve chambers 64 and the pressure-conduction chambers 62) in the cassette off from each other, while fluid is being pumped through the cassette. The cassette is used with a fixture which actuates the various valves in the cassette and applies pressure to the pressure-conduction chambers in the cassette. The sealing off of the interior walls 6 may be accomplished by the fixture when the cassette is placed in the fixture, by clamping the cassette between portions of the fixture so that the membrane 30 is pressed against the rigid interior walls 6. (The cassette being described herein functions like the cassette described in column 8, line 60, to column 9, line 18, of U.S. Pat. No. 5,088,515, referenced hereinabove. The cassette described therein has a rigid portion which is placed in a bag. The bag provides the membranes which perform the same function as the membranes of the disposable cassette being discussed herein.) Because pressing the flexible membrane 30 against the interior walls adequately seals off the fluid passageways, as long as it is thick enough (0.014 inch thick PVC has been used with good results), gaskets on the fixture are not necessary, but may be added to the fixture to further ensure that the fluid passageways are sealed off from each other.

A preferred embodiment of the fixture provides pressure to actuate the various valves 64 of the cassette and to provide gas pressure to the cassette's pressure-conduction chambers 62. In order to make the fixture face from which the gas is provided easy to wipe clean when liquid splashes on it, a sheet of silicone may be attached to the fixture face. The side of the silicone sheet facing the fixture may have projections thereon corresponding to the interior walls 6 of the cassette, i.e., a gasket integrally formed on the silicone on the fixture side of the silicone. However, an air pocket can form between the cassette's membrane 10 and the silicone sheet. This air pocket can interfere with the valving and measurement procedures performed by the fixture. To prevent an air pocket from forming between the cassette's membrane 30 and the fixture's silicone sheet, tiny holes may be punched through the silicone sheet using something like an intravenous needle, so as to form a tiny slit. A slit tends to open more easily to allow air to pass through than a pin hole. Even with these holes, the silicone sheet prevents liquid splashed on the silicone sheet from passing through the sheet, but the holes permit gas to pass through (e.g., when the fixture provides a negative pressure to pull the membrane 30 as far out as it can go).

As shown in the cross-section of the cassette depicted in FIG. 8, the interior walls 6 are lower than the perimeter wall 10. The interior walls 6 are made shorter so that they do not interfere with the welding process, or cut or weaken the membrane at points adjacent to the interior wall 6 during welding. The faces of the fixture against which the front and rear faces of the cassette are pressed must be shaped to accommodate the greater height of the perimeter wall 10, but must nevertheless be able to press the membrane 30 against the interior walls 6.

FIG. 9 shows a cross-section of the outer portion of a preferred embodiment of the disposable cassette's rigid. Because of the small scale, the energy directors are not shown in FIG. 9 or FIG. 8, but would be located at the front and rear ends 9 of the perimeter wall 10. Steps 8 are placed on the outside of the perimeter wall 10. These steps 8 may be used to hold the cassette in the proper position during welding of both sides of the cassette, during actual use of the cassette in the automated peritoneal dialysis system and during trimming of the membrane 30. During trimming, the membrane 30 is cut against this step 8 by a die-cutter, which is shaped to be just slightly larger than the outer perimeter of the cassette. The membrane 30 is not cut against the front or rear ends 19 of the wall 10, because trimming the membrane 30 too close to the weld point puts stress on the welded joint. (Welding and trimming may be performed in the same step by designing the front and rear ends 19 of the walls of the rigid portion 10 to further include a third ridge, which would have a blunt tip to act like a knife edge when the ultrasonic welder presses the membrane 30 against it, and which would be placed on the ledge 28 outside of and spaced away from the energy director 20. During the ultrasonic welding, this blunt ridge can cut all the way through the membrane 30 or weaken the membrane so that it may be torn off.)

Returning to FIGS. 1A and 1B, a ledge 28 (distinct from the step 8 shown in FIG. 9) is located adjacent the energy director 20 at the outer side of the perimeter wall This ledge 28 helps prevent the horn 40 from advancing too far during welding. It is important that the horn 40 does not advance too far, because otherwise the membrane 30 will tend to be cut by the horn 40 instead of just being welded to wall 10. In addition, as noted above, in order to further ensure that the horn does not cut the membrane 30, the horn must not remain on too long.

One problem encountered in prior art attempts to ultrasonically weld PVC with plasticizers is that the heat created during welding is believed to cause the plasticizers to migrate out of the membrane, causing the membrane to become brittle. Keeping the horn on for only a short period of time seems to minimize this migration.

The ledge 28 is placed on the outer side 11 of the wall 10 instead of the inner side 12, so as to prevent undesirable flashing—i.e., the spraying of melted material—into the interior of the cassette. An undue amount of flashing into the interior of the cassette can result in the undesirable situation of thermoplastic particulates being inside the cassette, where the parenteral fluid flows. Such undesirable flashing into the interior is reduced by having the inner ridge 22 slope all the way down to the inner side 12 of the wall 10. A small amount of flashing is desirable, if it forms a reasonably uniform bead at the corner where the membrane 30 meets the inner side 12 of the wall 10. It is preferable for the inner slope to go down below the level of the ledge 28, as shown in the energy director of FIG. 1B, because such a shape tends to result in a bead that is reasonably uniform and that does not protrude too far into the interior of the cassette. A bead is also desirable where the membrane 30 meets the outer side of the wall 10. Despite the advantages of having the ridge sides slope all the way down to the sides of the wall and the tendency of the ledge to create undesirable flashing, a ledge 28 is still important to ensure a proper weld, because, without the ledge 28, it is difficult to stop the welding at just the right time.

Figure 4:
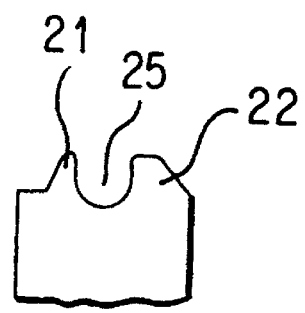
Figure 5:
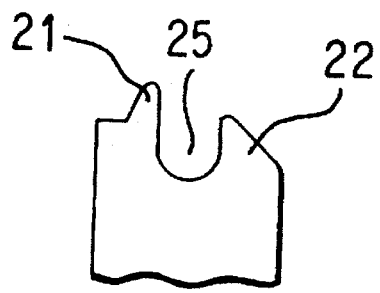

FIGS. 3–5 show several embodiments of the energy director 20. FIG. 3 shows the preferred embodiment of the energy director, which is also shown in FIG. 1B. FIG. 4, which depicts the-energy director shown in FIG. 1A, shows another preferred embodiment, which has been rigorously tested and found to be suitable for use in the disposable parenteral-fluid cassette shown in FIGS. 6–8. It is believed that the shorter ridges 21 and 22 and shallower groove 25 of the energy director of FIGS. 1A and 4 embodiment does not pinch on the membrane material in the groove 25 like the energy director of FIGS. 1B and 3. As can be expected from looking at the after-weld joints in FIGS. 2A and 2B, the FIG. 3 embodiment results in a joint that is somewhat more prone to peeling than the joint resulting from the FIG. 4 embodiment.

FIG. 5 shows an embodiment with a shorter inner ridge 22. The shorter inner ridge 22 may make the energy director less prone to particulate-generating flash directed towards the interior, but this design puts more of the sealing requirement on the outer ridge 21. In addition, although the FIG. 5 embodiment pinches the membrane material in the groove better than the embodiment shown in FIG. 4, the FIG. 5 embodiment is more prone to cutting the membrane during welding than either of the embodiments shown in FIGS. 3 and 4.

An embodiment of the energy director having three or more ridges may for some applications be beneficial. Like the embodiment having only two ridges, a three-ridged energy director slows down the weld time (as compared to a single-ridged energy director) and, in fact, should slow it down even more than a two-ridged energy director. The disadvantage of an energy director having three or more ridges is that the energy being imparted by the horn 40 is divided amongst the three or more ridges. Thus, less energy is available to melt the rigid material making up the energy director than in a two-ridged energy director. This reduction in the energy available to each ridge can be a serious disadvantage if there is a significant difference in the melting temperatures of the two materials being welded together. Another disadvantage of having more than two ridges is that the ridge of ridges between the two outer ridges can inhibit the flow of the melted rigid material towards the middle of the energy director.

Using only a single ridge has several disadvantages. As noted above, a single-ridged energy director does not slow down the welding and therefore does not give greater tolerance for the welding parameters like a two-ridged energy director. In addition, a single-ridged energy director is generally more fragile than a two-ridged energy director. Since typically the horn is moving when it comes into contact with the membrane, which lies on top of the energy director, the impact of the horn could break a single-ridged energy director. Thickening the single ridge to make it less fragile makes it more difficult to melt the rigid material forming the energy director, which could result in the membrane being too thin or being cut as a result of the welding.

A single-ridged energy director may, nevertheless, be useful in some situations, such as when the two materials to be welded together are more compatible. If it results in a sufficiently strong weld, a single-ridged energy director may be desirable to avoid the greater cost involved in molding a two-ridged energy director. By using some of the features discussed herein, the joint formed with a single-ridged energy director may be improved. Such an improved single-ridged energy director is shown in FIG. 10. Using a ledge 28, such as that shown in FIGS. 1A, 1B, and 3–5, as well as in FIG. 10, helps stop the welding at the correct time. Having the inner side of the single ridge slope down all the way to inner side 12 of the wall, like the right side of the inner ridges 22 shown in FIGS. 1A, 1B, 3–5 and 10, provides a joint resistant to peeling from the inner side 12 to the outer side 11 (such as when the membrane on the cassette is being distended). Having the inner slope meet the wall's inner side 12 at a point below the ledge 28, like the right side of the inner ridges 22 shown in FIGS. 1B, 3, 5 and 10, provides a joint even more resistant to peeling from the inside. Furthermore, as compared to prior-art single-ridged energy directors, the energy director shown in FIG. 10 can provide the right amount of flashing to have a strong bond between the membrane and the rigid portion, without undesirable particulate-generating flashing towards the interior of the cassette. As noted above, despite the advantages of having the ridge sides slope all the way down to the sides of the wall, a ledge 28 is still important to ensure a proper weld, because, without the ledge 28, it is difficult to stop the welding at just the right time.

The present invention provides a joint that can be made through a simple, relatively inexpensive process, that avoids creating particulate matter in the interior of a cassette, that can function as a hermetic seal, and that is stable even during fairly rigorous sterilization procedures, such as ethylene oxide sterilization. Many solvent bonds tend to deteriorate during ethylene oxide sterilization. Ultrasonically welding the membranes to the rigid portion of a cassette provides advantages over the cassette discussed in U.S. Pat. No. 5,088,515, where the rigid portion is placed in a bag. A cassette with ultrasonically bonded membranes is easier to locate properly in a fixture. It is also easier to attach tubes to the nozzles 51–55 of such a cassette.

What is claimed is:

1. An energy director for use on a surface which is to be ultrasonically welded to a second thermoplastic piece of material, the surface having a length, the energy director comprising:

a first ridge running the length of the surface;

a second ridge running the length of the surface and substantially parallel to the first ridge; and a groove running the length of the surface between the first and second ridges, wherein the energy director is made of a thermoplastic material, wherein both the first and second ridges have a first side adjacent the groove and a second side opposite the groove the first side of both ridges directly face each other across the groove, wherein the first ridge's first side is steeper than the first ridge's second side, wherein the second ridge's first side is steeper than the second ridge's second side, and wherein the ridges and the groove are shaped so as to promote flow of the thermoplastic material toward the groove during ultrasonically welding.

2. An energy director according to claim 1, wherein the surface is located at the end of a wall, the wall having a side, and where the second ridge's second side slopes all the way down to the side of the wall.

3. An energy director according to claim 2, further including a ledge, adjacent the first ridge's second side.

4. An energy director according to claim 3, wherein the second ridge's second side slopes down to a point below the ledge.

* * * * *

UNITED STATES PATENT AND TRADEMARK OFFICE
CERTIFICATE OF CORRECTION

PATENT NO. : 5,540,808
DATED : July 30, 1996
INVENTOR(S) : Douglas E. Vincent

It is certified that error appears in the above-indentified patent and that said Letters Patent is hereby corrected as shown below:

Title page, item [54] and col. 1, lines 2 and 3, delete "And Joint Produced Thereby"

Col. 10, line 38, insert a comma after "groove"
Col. 10, line 46, change "ultrasonically" to --ultrasonic--

Signed and Sealed this

Fourteenth Day of January, 1997

Attest:

BRUCE LEHMAN

Attesting Officer

Commissioner of Patents and Trademarks